(12) United States Patent
Todorov et al.

(10) Patent No.: US 10,234,426 B2
(45) Date of Patent: Mar. 19, 2019

(54) MATRIX PHASED ARRAY SYSTEM FOR ULTRASONIC INSPECTION OF BRAZED WELDS

(71) Applicant: EDISON WELDING INSTITUTE, INC., Columbus, OH (US)

(72) Inventors: Evgueni I. Todorov, Loveland, CO (US); Roger L. Spencer, Ashville, OH (US); Lance S. Cronley, Mt. Victory, OH (US)

( * ) Notice: Subject to any disclaimer, the term of this patent is extended or adjusted under 35 U.S.C. 154(b) by 0 days.

(21) Appl. No.: 15/912,831

(22) Filed: Mar. 6, 2018

(65) Prior Publication Data
US 2018/0196010 A1 Jul. 12, 2018

Related U.S. Application Data

(63) Continuation of application No. 14/970,054, filed on Dec. 15, 2015, now abandoned.
(Continued)

(51) Int. Cl.
G01N 29/06 (2006.01)
G01N 29/11 (2006.01)
G01N 29/26 (2006.01)

(52) U.S. Cl.
CPC .......... *G01N 29/0645* (2013.01); *G01N 29/11* (2013.01); *G01N 29/262* (2013.01);
(Continued)

(58) Field of Classification Search
CPC .......... G01N 2291/106; G01N 29/262; G01N 29/2456; G01N 29/221; G01N 29/0645;
(Continued)

(56) References Cited

U.S. PATENT DOCUMENTS 2,404,391 A * 7/1946 Mason .................. B06B 1/0629
333/138
3,543,065 A * 11/1970 Phelan ............... G01N 29/2437
310/336
(Continued)

FOREIGN PATENT DOCUMENTS

GB        2409039 A  *  6/2005  .......... G01N 29/223
WO   WO-2012103628 A1 *  8/2012  .......... G01N 29/069
WO   WO 2014/001962 A1    1/2014

OTHER PUBLICATIONS

International Search Report and Written Opinion for International Application No. PCT/US2015/065841, 12 pages.
(Continued)

*Primary Examiner* — Daniel S Larkin
*Assistant Examiner* — David L Singer
(74) *Attorney, Agent, or Firm* — Frost Brown Todd LLC

(57) ABSTRACT

A system for non-destructively inspecting brazed joints that includes at least one matrix phased array probe that further includes plurality of ultrasonic transducer elements arranged in an array at one end of the probe, wherein the transducer elements are operative to both generate ultrasonic signals and to receive reflections thereof; and at least one tip adapted to be removably mounted over the array of ultrasonic transducer elements, wherein a region of the at least one tip has been shaped to correspond to the geometric characteristics of an item or a specific portion of an item that includes a brazed joint to be inspected; and a processor running software that includes at least one imaging algorithm for processing data received from the at least one matrix phased array probe and generating color coded ultrasonic C-scan images of inspected brazed joints.

8 Claims, 6 Drawing Sheets

Related U.S. Application Data

(60) Provisional application No. 62/091,869, filed on Dec. 15, 2014.

(52) U.S. Cl.
CPC ............... *G01N 2291/0234* (2013.01); *G01N 2291/044* (2013.01); *G01N 2291/106* (2013.01); *G01N 2291/267* (2013.01)

(58) Field of Classification Search
CPC ..... G01N 29/11; G01N 2291/267–2291/2677; G01N 2291/2691; G01N 2291/223; G10K 11/34; B06B 1/0622; B06B 1/0629; A61B 8/4411
USPC .......... 73/628, 620, 625–626, 602, 632, 633, 73/641, 642, 588; 702/39
See application file for complete search history.

(56) References Cited

U.S. PATENT DOCUMENTS

| | | | | |
|---|---|---|---|---|
| 3,596,504 A * | 8/1971 | Frey | ............... | G01N 29/221 73/626 |
| 4,208,917 A * | 6/1980 | Aoyama | ............... | G01N 29/221 73/588 |
| 4,455,873 A * | 6/1984 | Abts | ............... | G01N 29/032 73/629 |
| 5,721,380 A * | 2/1998 | Gozlan | ............... | G01N 29/223 73/761 |
| 5,957,850 A | 9/1999 | Marian, Jr. et al. | | |
| 6,276,212 B1 * | 8/2001 | Cooper | ............... | G10K 9/122 310/324 |
| 2002/0138007 A1 * | 9/2002 | Nguyen-Dinh | ............... | A61B 8/00 600/459 |
| 2006/0283250 A1 | 12/2006 | Fair et al. | | |
| 2008/0161688 A1 | 7/2008 | Poland | | |
| 2008/0194951 A1 * | 8/2008 | Poland | ............... | A61B 8/00 600/437 |
| 2009/0133501 A1 * | 5/2009 | Georgeson | ............... | G01N 29/04 73/632 |
| 2010/0031750 A1 * | 2/2010 | Spencer | ............... | G01N 29/069 73/620 |
| 2010/0191123 A1 * | 7/2010 | Tsung | ............... | A61B 8/12 600/463 |
| 2010/0236330 A1 * | 9/2010 | Nyholt | ............... | G01N 29/223 73/644 |
| 2011/0209542 A1 * | 9/2011 | Hucker | ............... | G01P 5/00 73/273 |
| 2011/0296923 A1 * | 12/2011 | Cataldo | ............... | G01N 29/043 73/632 |
| 2012/0006132 A1 | 1/2012 | Faucher et al. | | |
| 2012/0137779 A1 * | 6/2012 | Graff | ............... | G01N 29/2487 73/632 |
| 2012/0310551 A1 * | 12/2012 | Na | ............... | G01N 29/0645 702/39 |
| 2012/0318038 A1 * | 12/2012 | Spigelmyer | ............... | G01H 1/00 73/1.82 |
| 2013/0187671 A1 | 7/2013 | Widhalm | | |
| 2014/0165730 A1 | 6/2014 | Na et al. | | |
| 2014/0265728 A1 | 9/2014 | Li et al. | | |
| 2015/0253288 A1 | 9/2015 | Spencer et al. | | |
| 2016/0169840 A1 | 6/2016 | Todorov et al. | | |

OTHER PUBLICATIONS

ASTM International, E2700-09 Standard Practice for Contact Ultrasonic Testing of Welds Using Phased Arrays.

Fahr, Ultrasonic C-Scan Inspection of Composite Materials, Jan. 1992.

Ikeda et al, Development of New Ultrasonic Inspection Technique for Spot Welds with Matrix Arrayed Probe and Shaft, Welding in the World, vol. 60, No. 5/6, 2006.

Karasawa et al, 3D-SAFT Ultrasonic Inspection Equipment "Matrixeye™", 2009.

Laminated Plastics, Technical Data Sheet Rexolite.

Na, Nondestructive Inspection of Resistance Spot Welds Using Matrix Phased Array Ultrasonic Technology, Advanced Materials & Processes, Mar. 2014.

Na et al, Design and Development of Idgh Frequency Matrix Phased-Array Ultrasonic Probes, Review of Progress in Quantitative Nondestructive Evaluation A1 P Conf. Proc. 1430, 905-912 (2012).

Toshiba, "Matrixeye™", Mar. 2011.

* cited by examiner

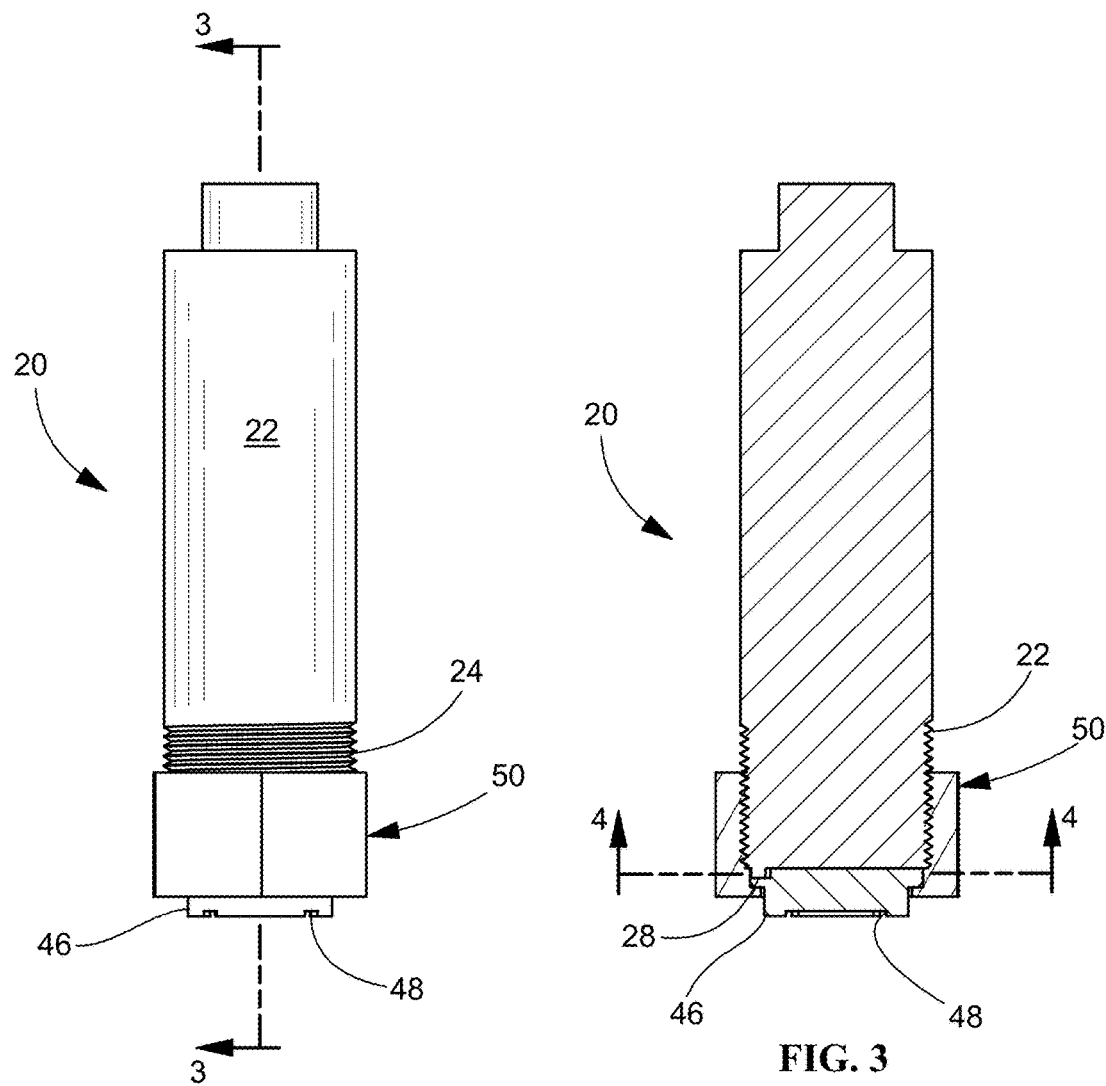
FIG. 2
FIG. 3
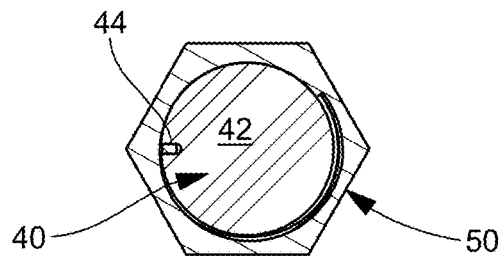
FIG. 4

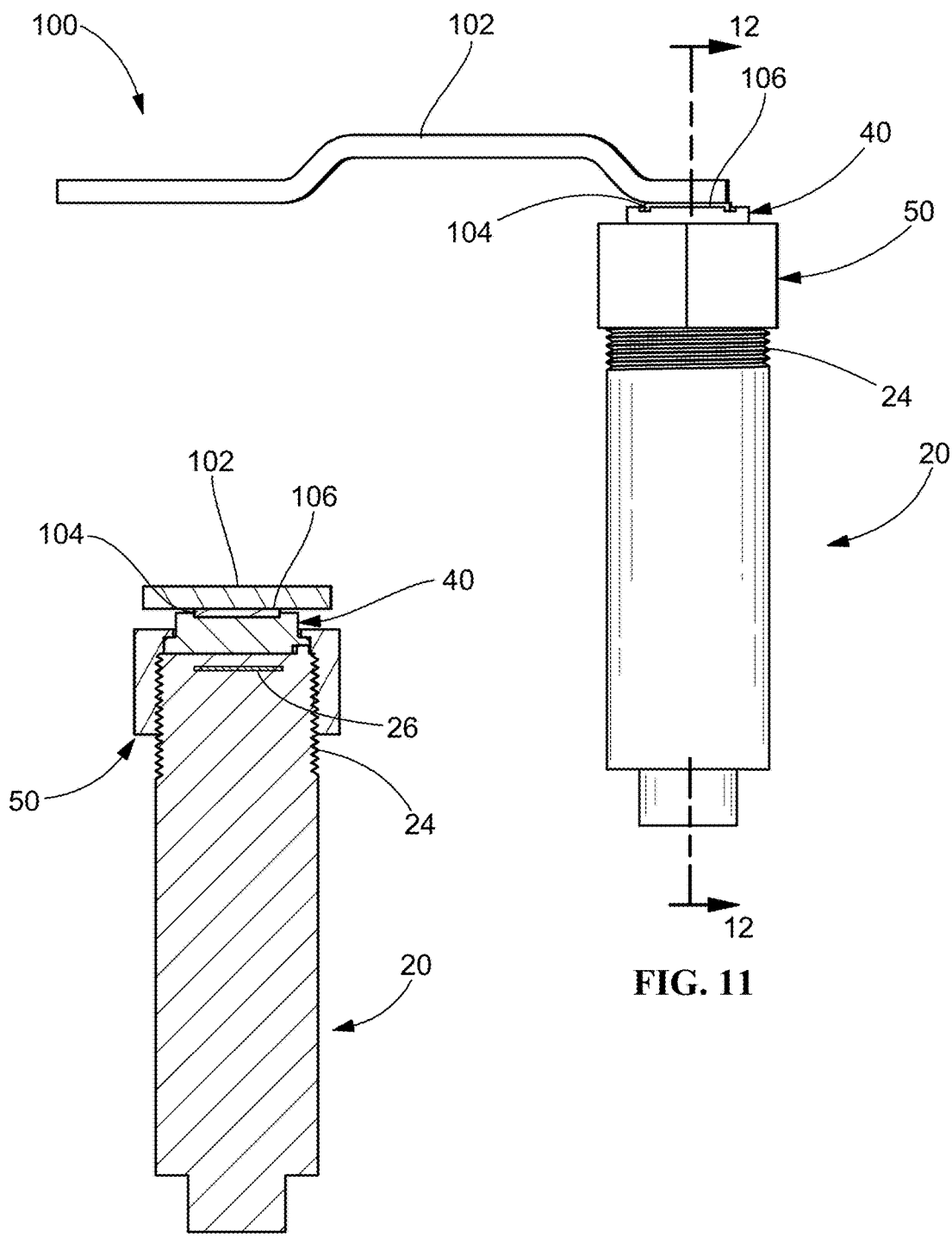

MATRIX PHASED ARRAY SYSTEM FOR ULTRASONIC INSPECTION OF BRAZED WELDS

CROSS-REFERENCE TO RELATED APPLICATIONS

This patent application is a continuation of U.S. patent application Ser. No. 14/970,054 filed on Dec. 15, 2015 and entitled "Matrix Phased Array System for Inspection of Brazed Welds", which claimed the benefit of U.S. Provisional Patent Application Ser. No. 62/091,869 filed on Dec. 15, 2014 and entitled "Matrix Phased Array System for Inspection of Brazed Welds", the disclosures of which are hereby incorporated by reference herein in their entirety and made part of the present U.S. utility patent application for all purposes.

BACKGROUND OF THE INVENTION

The present invention relates generally to inspection systems for use in assessing the performance of industrial manufacturing processes, and more specifically to a nondestructive inspection system for assessing the quality of brazed joints and fusion or solid-state sheet metal joints.

Sheet metal joining processes are widely used in many industries including the aerospace and automotive industries. Resistance spot welding, seam welding, weld bonding, adhesive joining, soldering, and brazing are used for various applications in different industries. Among these processes, the brazing procedure is used to join metal sheets where good electrical conductivity, as well as mechanical and thermal strength, is required from the joint. The quality control of such joining processes has been recognized as an important issue to manufacturers. The quality of brazed joints is affected by the joining process itself and by the design of the joint. Many factors are considered, including metallurgic reaction conditions; thermal behaviors; chemical composition; starting condition of the base metal; brazing and bonding conditions; and the particular brazing and bonding equipment used during the process. Furthermore, the intricate relationship between these factors makes it difficult to control the quality of the brazed joint and difficult to inspect the weld joint in a nondestructive manner. It is particularly difficult to inspect on-line small areas such as electrical contacts brazed to terminal or arm sheet metal conductors due to the strong geometry and edge effects presented by such items.

Certain acoustic methods enable nondestructive testing of welded parts that is useful for various inspection applications. Unlike other nondestructive testing methods, acoustic methods provide both surface and internal information about a particular weld joint. Moreover, acoustic methods allow for deeper penetration into test specimens and provide higher sensitivity regarding small discontinuities that may be present in a weld joint. Acoustic methods, however, do have limitations, including the requirement of having a skilled and knowledgeable operator for using a test device and then analyzing acoustic data derived from a test specimen. Accordingly, the field of ultrasonic nondestructive evaluation (NDE) is in need of a reliable process or technique for identifying poor quality brazed joints in a manner that eliminates the requirement of a skilled operator and the subjective interpretation of test data.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first system for non-destructively inspecting brazed welds or brazed joints is provided. This system includes at least one matrix phased array probe that further includes a plurality of ultrasonic transducer elements, arranged in an array at one end of the probe, that are operative to both generate ultrasonic signals and to receive reflections thereof; and at least one tip adapted to be removably mounted over the array of ultrasonic transducer elements, wherein a region of the at least one tip has been shaped to correspond to the geometric characteristics of an item or a specific portion of an item that includes a brazed joint to be inspected; and a processor running software that includes at least one imaging algorithm for processing data received from the at least one matrix phased array probe and generating A-scans and color coded C-scan images of inspected brazed joints.

In accordance with another aspect of the present invention a second system for non-destructively inspecting brazed welds or brazed joints is provided. This system includes a phased array control unit; at least one matrix phased array probe connected to the phased array control unit, wherein the matrix phased array probe further includes a plurality of ultrasonic transducer elements, arranged in an array at one end of the probe, that are operative to both generate ultrasonic signals and to receive reflections thereof; and at least one tip adapted to be removably mounted over the array of ultrasonic transducer elements, wherein a region of the at least one tip has been formed or shaped to correspond to the geometric characteristics of an item or a specific portion of an item that includes a brazed joint to be inspected; a processor running software that includes at least one imaging algorithm for processing data received from the at least one matrix phased array probe and generating A-scans and color coded C-scan images of inspected brazed joints; and at least one monitor for visually displaying the A-scans and color coded C-scan images of inspected joints in real time.

In yet another aspect of this invention, a third system for non-destructively inspecting brazed welds or brazed joints is provided This system includes a phased array control unit; at least one matrix phased array probe connected to the phased array control unit, wherein the matrix phased array probe further includes a plurality of ultrasonic transducer elements arranged in an array at one end of the probe, wherein the transducer elements are operative to both generate ultrasonic signals and to receive reflections thereof; and at least one tip adapted to be removably mounted over the array of ultrasonic transducer elements, wherein a region of the at least one tip has been shaped to correspond to the geometric characteristics of an item or a specific portion of an item that includes a brazed joint to be inspected; an enclosure that may be portable or that may be designed to be placed on a flat surface and that includes at least one input for connecting to the at least one matrix phased array probe; ultrasonic phased array transmitting and receiving circuitry in electrical communication with the at least one input; and at least one external mount for supporting the matrix phased array probe; a processor running software that includes at least one imaging algorithm for processing data received from the at least one matrix phased array probe and generating A-scans and color coded C-scan images of inspected brazed joints; and at least one monitor for visually displaying the A-scans and color coded ultrasonic C-scan images of inspected joints in real time.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIG. 2 is a side view of the matrix phased array probe of FIG. 1, shown in its assembled state;

FIG. 3 is cross-sectional side view of the matrix phased array probe of FIG. 2;

FIG. 4 is a cross-sectional top view of a section of the matrix phased array probe of FIG. 2 showing the tip and orientation slot aspects of the matrix phased array probe;

FIG. 11 is a side view of the matrix phased array probe of FIG. 2 in contact with a test specimen having a braze weld joint to be analyzed;

FIG. 12 is a cross-sectional front view of the assembly of FIG. 11;

DETAILED DESCRIPTION OF THE INVENTION

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides a matrix phased array (MPA) inspection system for non-destructive (NDE) evaluation of brazed weld joint and other types of weld joints. The exemplary embodiment of this inspection system shown in the Figures and described herein uses high frequency (12 MHz) ultrasonic energy to determine the area of lack of braze (LOB) in flat brazed contacts. This system typically includes the following basic components; (i) a matrix phased array probe; (ii) one or more removable tips that are mounted on the probe during weld joint analysis; (iii) a phased array unit to which the probe is connected; (iv) a processor connected to the phased array unit and running specific software for processing and analyzing data generated by the phased array unit; and (v) a monitor for visualizing A-scans and C-scans generated by the software. The phased array unit and other system components associated with the phased array unit may be assembled in an enclosure that includes a fixed bracket for holding the matrix phased array probe during the evaluation of test specimens.

Figure 1:
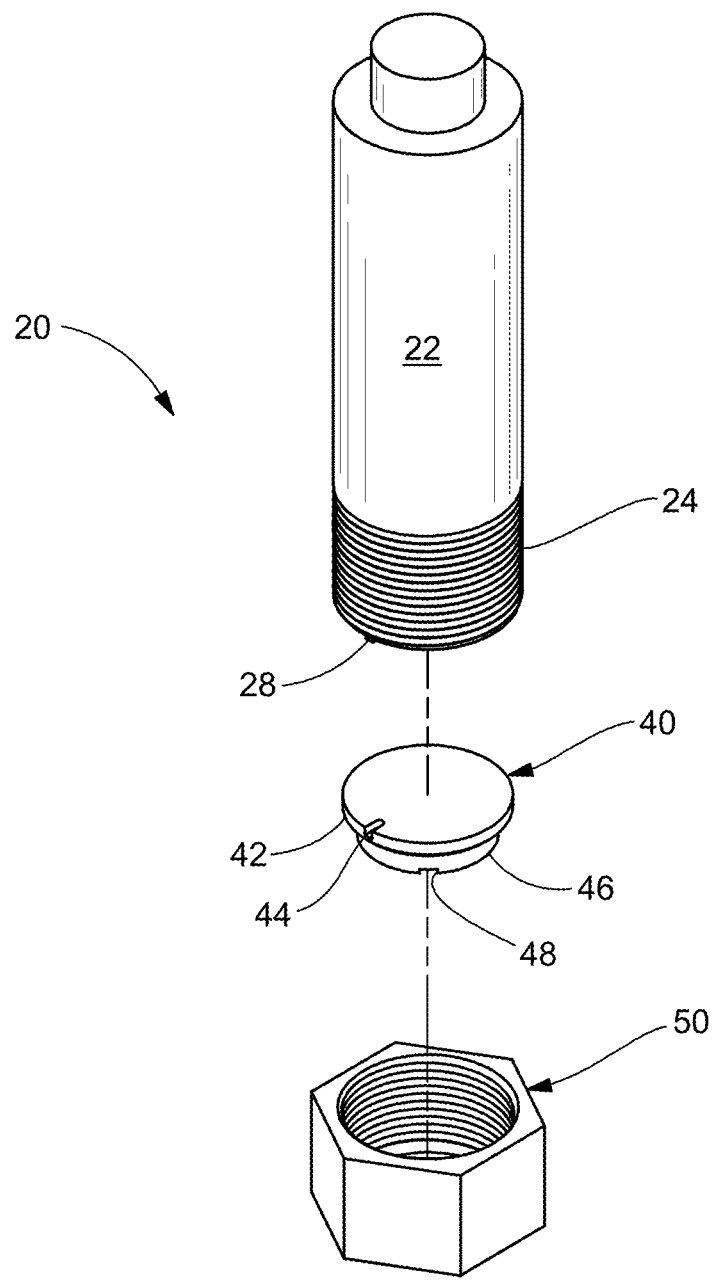
FIG. 1 is an exploded view of a matrix phased array probe, in accordance with an exemplary embodiment of the present invention.
Figure 5:
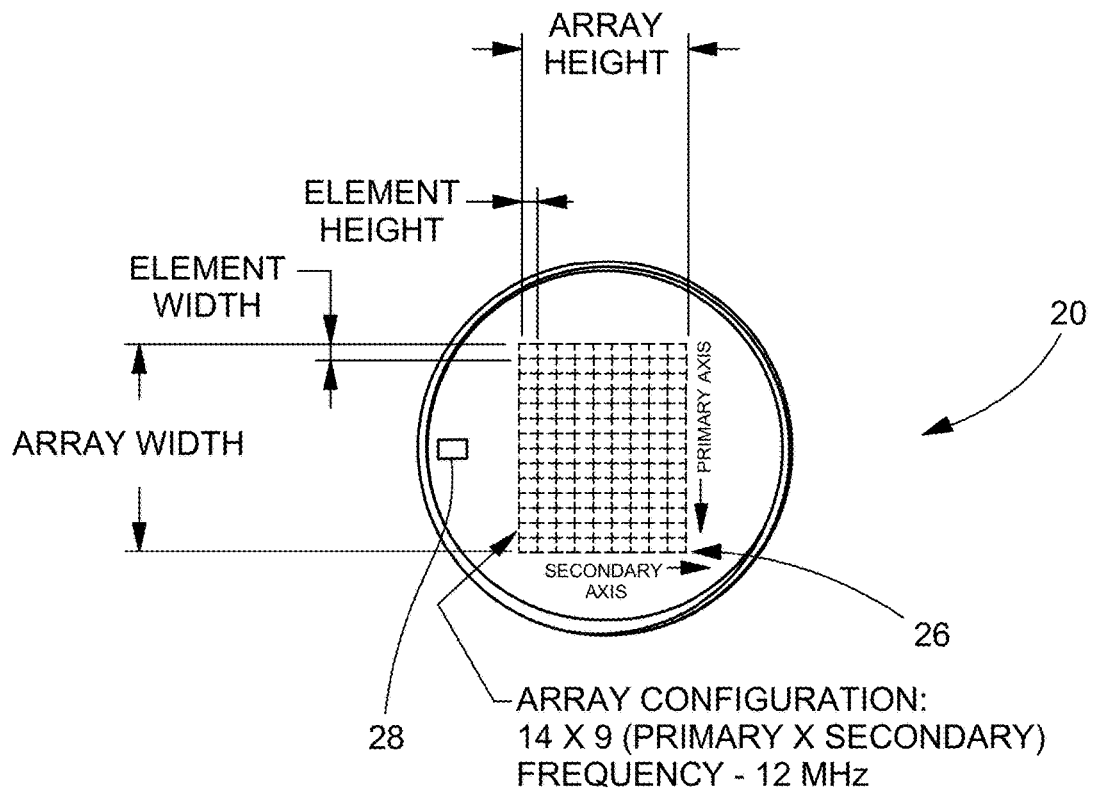
FIG. 5 is a bottom view of an exemplary embodiment of the matrix phased array probe of the present invention showing the layout and appearance of the sensor array.
Figure 6:
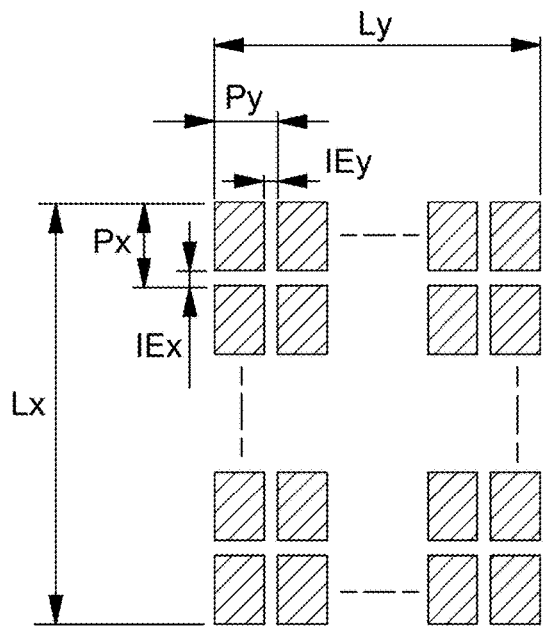
FIG. 6 is a schematic of the sensor array of the matrix phased array probe of the present invention illustrating certain relevant dimensions of the array.
Figure 7:
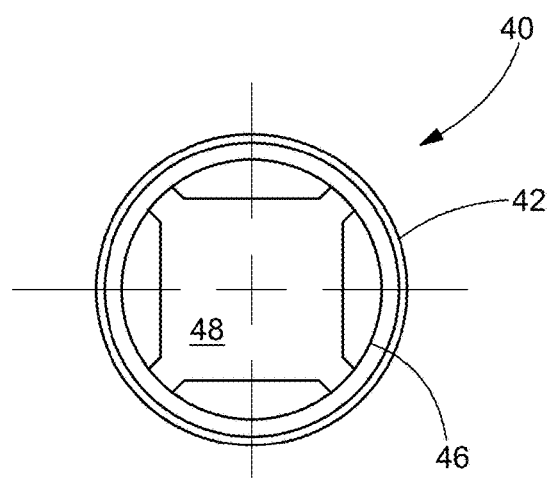
FIG. 7 is a front view of the tip component of the present invention.
Figure 8:
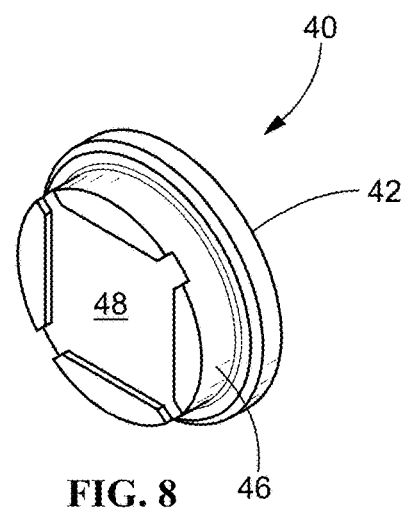
FIG. 8 is a perspective view of the tip component of FIG. 7.
Figure 9:
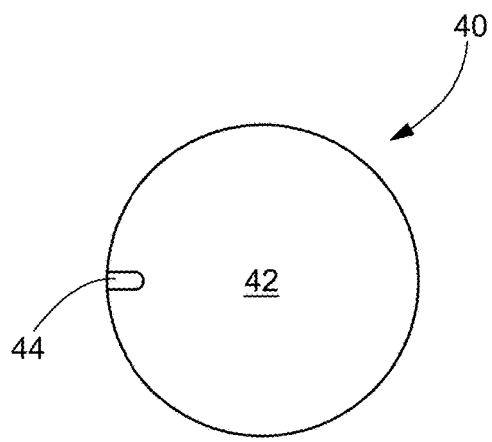
FIG. 9 rear view of the tip component of FIG. 7.

FIGS. 1-4 provide various illustrative views of a matrix phased array probe, in accordance with an exemplary embodiment of the present invention. Matrix phased array (MPA) probe 20 includes cylindrical probe housing 22, threaded region 24, sensor array 26, and orientation pin 28. With reference to FIGS. 5-6, in this embodiment, MPA probe 20 includes two-dimensional (2-D) matrix array 26 having the following characteristics: (i) number of channels (Nx×Ny): 14×9 elements; (ii) pitch in primary axis (Px): 0.8 mm; (iii) pitch in secondary axis (Py): 1.0 mm; (iv) inter-element spacing (IEx): 0.1 mm; (v) inter-element spacing (IEy): 0.1 mm; (vi) element height: 0.9 mm; (vii) element width 0.7 mm; (viii) total active area (Lx×Ly): 11.1×8.9 $mm^2$; (ix) center frequency: 12 MHz; and (x) acoustical impedance matching (for tip 40): thermoset cross-linked styrene copolymer tip (e.g., Rexolite®). In other embodiments, the inter element spacing for IEx and IEy is about 0.5 mm.

Figure 10:
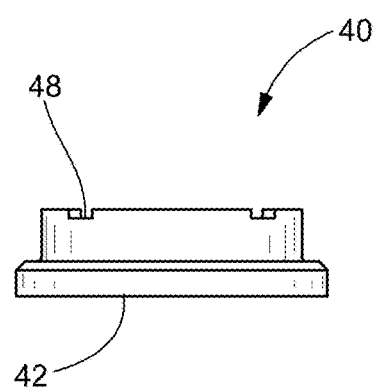
FIG. 10 is a side view of the tip component of FIG. 7.
Figure 13:
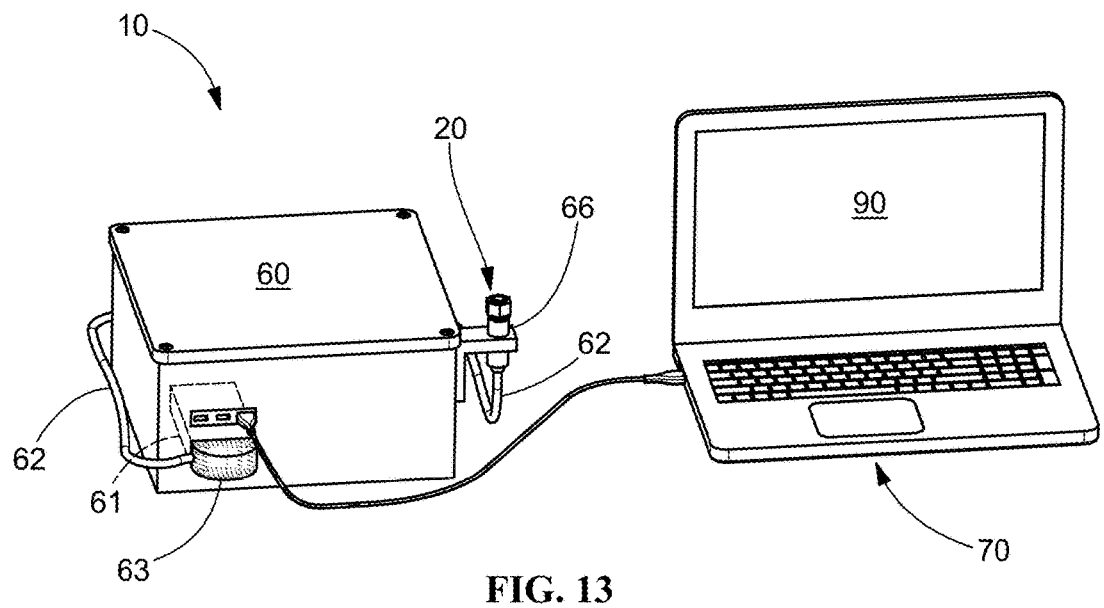
FIG. 13 is a drawing of the matrix phased array NDE system of the present invention.
Figure 14:
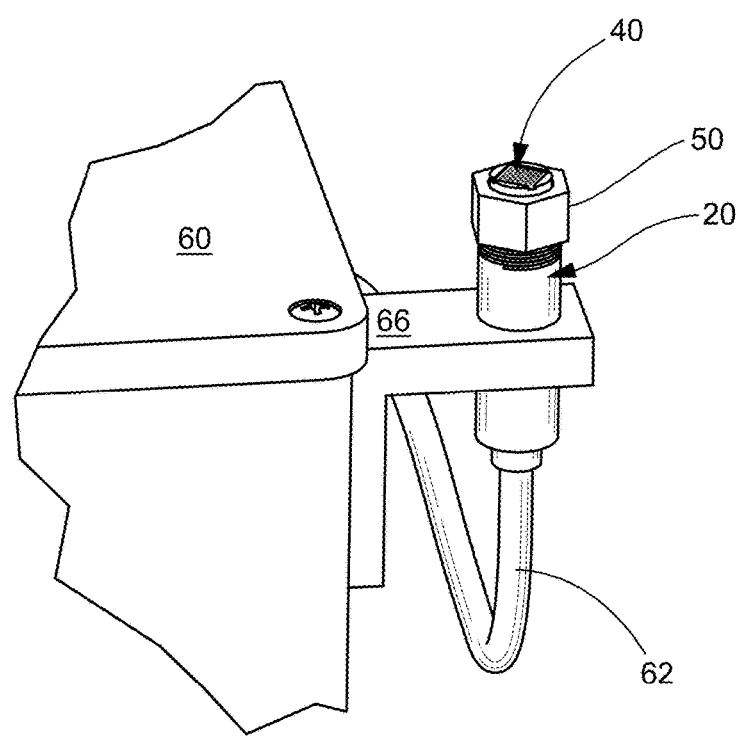
FIG. 14 is a close-up drawing of the probe and bracket components of the matrix phased array NDE system of FIG. 13.

As shown in FIGS. 10, an exemplary embodiment of plastic cylindrical tip 40 includes base 42; orientation slot 44, which cooperates with orientation pin 28 for properly aligning tip 40 on the end of MPA probe 20; tip body 46, upon which various identifying indicia may be placed; and recess 48, the geometry of which has been adapted to match or closely cooperate with the shape of a specific flat terminal contact that has been braze welded to a terminal body. As shown in FIGS. 11-12, an exemplary part to be inspected 100 includes terminal body 102 and terminal contact 104, which has a specific geometry that corresponds to the geometry of recessed area 48 in tip 40. During evaluation, probe 20 is inverted and mounted within bracket 66, which is typically mounted on one side of enclosure 60, as shown in FIGS. 13-14. Sensor array 26 is coated with acoustic couplant gel, tip 40 is placed over sensor array 26 on MPA probe 20, and locking member (nut) 50 is tightened onto threaded region 24 to secure tip 40 to the tip of MPA probe 20. Part 100 is then positioned such that terminal contact 104 is seated within recessed area 48 of tip 40. Phased array unit (PAU) 61 and sensor array 26 are then activated for the purpose evaluating the braze weld between terminal body 102 and terminal contact 104. Tip 40, and particular the shape and other geometric characteristics of recessed area 48, which is formed in body 46 of tip 40, may be modified to fit any number of different contacts (or other structures) that a brazed welded to terminal bodies or other items. Accordingly, a great many variants of tip 40 are possible.

As shown in FIGS. 13-14, ultrasonic multi-channel cable 62 with Ipex connector 63 is used for connecting MPA probe 20 to phased array unit 61 (32/128: Advanced OEM Solutions), which is housed within enclosure 60. Suitable enclosures include Carlon® types 1 and 2, and other components included in the enclosure typically include a cooling fan (e.g., 4" AC Brushless, 115 VAC, Rotation Speed 2100 RPM, Airflow 65 CFM, 119×119×38 mm, Mounting holes 4.2 mm.); a switch mode power supply (e.g., Model— ETSA240270UD; P/N—ETSA240270UDC-P5P-SZ; Input—100-240V~, 50-60 Hz, 1.5 A; Output—24V 2.7 A); and a relocatable power tap (e.g., model UTPB 1115 (YLPT-22A); Maximium Load—15 A, 125 VAC, 60 Hz). Serial cable 64 is used to connect phased array unit 61 to processor 70, which is typically a laptop or desktop computer that is connected to a monitor 90. Processor 70 runs software that that includes at least one imaging algorithm for processing data received from MPA probe 20 and generating color coded ultrasonic C-scan images of characterized brazed weld, as well as other drivers to control phased array unit 61 and the data acquisition process. An example of suitable imaging software is SpotSight®, which is available from EWI, Inc. (Columbus, Ohio).

When inspection system 10 is in use, recessed area 48 centers terminal contact 104 with respect to the rectangular area coverage of sensor array 26. Recessed area 48 permits slight movements along the length and width thereof to maximize LOB indications, if present. If an LOB indication is present that exceeds a predetermined threshold on the A-scan, it will be imaged in red color on the C-scan. Indications with amplitude smaller than the predetermined threshold are imaged in blue or other colors. The threshold is adjusted so that only the area of the brazed joint 106 between terminal contact 104 and terminal body 102 is tested and imaged. The elements of MPA probe 20 are interrogated in a predetermined sequence to cover the entire area under the probe. The areas where the signal is larger than the threshold are summed to determine the total LOB area. It is displayed as absolute value in mm$^2$ and relative percent (%) of the region of interest. An area or region of interest is specified for each terminal contact 104 as shown on the C-scan. The MPA area coverage is designed for the largest contact area. Other contacts 104 that are smaller in size are tested by selecting an appropriate tip 40 and recessed area 48 that fits the contact and adjusting the region of interest on the C-scan so that the same probe can be used to test all contact sizes. A single percentage LOB acceptance criterion can be specified for all contacts 104 regardless of their size. The C-scan image with measured LOB is captured and stored for reporting purposes. A determination of weld integrity is based on whether sound passes through the brazed weld or not. Algorithms included in the SpotSight® software assist in generating both an A-scan and a color (red/green/yellow) representation of the welded region, which is a C-scan. Each part to be inspected 100 typically receives a custom tip 40 and some applications of this invention utilize a flexible probe membrane.

Advantageously, exemplary embodiments of the system of the present invention includes (i) a fixed sensor; (ii) numerous tips with recessed areas or slots to guide and center various contacts; (iii) regions of interest are specified on a C-scan; (iv) a single sensor may be used for all contact sizes; (v) a region of interest can also be used when several elements of the MPA probe are grouped to focus and steer the ultrasonic beam for contacts that have curved surfaces as opposed to flat contacts.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A system for non-destructively inspecting brazed joints, comprising:
    (a) an item, wherein the item includes a brazed joint to be inspected, and wherein the braze joint to be inspected has a specific raised geometry;
    (b) at least one matrix phased array probe, wherein the matrix phased array probe further includes:
        (i) a plurality of ultrasonic transducer elements arranged in an array at one end of the probe, wherein the transducer elements are operative to both generate ultrasonic signals and to receive reflections thereof;
        (ii) an orientation pin positioned adjacent to the plurality of ultrasonic transducer elements; and
        (iii) at least one tip adapted to be removably mounted over the array of ultrasonic transducer elements,
            a) wherein the at least one tip includes a recessed area formed therein that matches or closely cooperates with the specific raised geometry of the brazed joint to be inspected, and
            b) wherein the at least one tip includes an orientation slot that cooperates with the orientation pin for properly orienting the tip over the plurality of ultrasonic transducer elements; and
    (c) a processor running software that includes at least one imaging algorithm for processing data received from the at least one matrix phased array probe and generating A-scans and color-coded C-scan images of inspected brazed joints.

2. The system of claim 1, further comprising at least one phased array control unit in electrical communication with the at least one matrix phased array probe.

3. The system of claim 1, further comprising at least one monitor for visually displaying the color coded ultrasonic C-scan images of inspected joints in real time.

4. The system of claim 1, further comprising an enclosure, wherein the enclosure is designed to be placed on a flat surface, and wherein the enclosure includes:
    (a) at least one input for connecting to the at least one matrix phased array probe;
    (b) ultrasonic phased array transmitting and receiving circuitry in electrical communication with the at least one input; and
    (c) at least one external mount for supporting the matrix phased array probe.

5. The system of claim 1, further comprising a locking member, wherein the locking member is adapted to secure the at least one tip to the at least one matrix phased array probe.

6. The system of claim 1, wherein the at least one matrix phased array probe is a two-dimensional probe and the array of ultrasonic transducer elements is a 14×9 configuration.

7. The system of claim 1, wherein the tip is manufactured from a thermoset cross-linked styrene copolymer.

8. The system of claim 1, wherein the item that includes a brazed joint to be inspected is an electrical terminal that includes a contact portion braze welded to a body portion.

* * * * *